United States Patent [19]

Barcza

[11] 4,297,349
[45] Oct. 27, 1981

[54] SILICON-BEARING CARBOXYLIC ACIDS AND AMIDES

[75] Inventor: Sandor Barcza, Mt. Lakes, N.J.

[73] Assignee: Sandoz, Inc., E. Hanover, N.J.

[21] Appl. No.: 140,562

[22] Filed: Apr. 15, 1980

[51] Int. Cl.$^3$ .......................... A01N 55/00; C07F 7/10
[52] U.S. Cl. .................... 424/184; 556/419; 260/404; 260/326.13 R; 260/326.13 A; 260/326.13 B; 260/326.13 C; 260/326.13 D
[58] Field of Search ...... 556/419; 260/404, 326.13 A, 260/326.13 B, 326.13 R, 326.13 C, 326.13 D; 424/184

[56] References Cited

U.S. PATENT DOCUMENTS

| | | | |
|---|---|---|---|
| 2,610,199 | 9/1952 | Sommer | 556/419 UX |
| 2,629,727 | 2/1953 | Speier | 556/419 UX |
| 2,894,967 | 7/1959 | Gilkey | 556/419 UX |
| 2,973,383 | 2/1961 | Black | 556/419 |
| 3,068,152 | 12/1962 | Black | 556/419 |
| 3,529,007 | 9/1970 | Brison | 556/419 UX |
| 3,651,115 | 3/1972 | Belsky et al. | 260/448.2 |
| 3,657,147 | 4/1972 | Poal et al. | 556/419 UX |
| 3,995,059 | 11/1976 | Fukumaru et al. | 424/324 |

FOREIGN PATENT DOCUMENTS 8130  2/1980  European Pat. Off.
2012261  7/1979  United Kingdom.

Primary Examiner—Paul F. Shaver
Attorney, Agent, or Firm—GeraldD. Sharkin; Richard E. Vila; Frederick H. Weinfeldt

[57] ABSTRACT

The final products are compounds of the formula

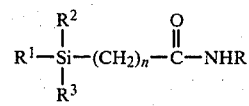

wherein
(a) each of $R^1$, $R^2$ and $R^3$ alkyl having from 1 to 22 carbon atoms; or
(b) one or more is a phenyl or alkylphenyl type, n is from 3 to 20; and
R is of an aralkyl-, phenyl-tryptophanyl- or benzocycloalkyl-type, eg D,L-5,5-dimethyl-5-sila-pentadecanoyl-1'-phenyl-2'-p-tolyl-ethylamide, are useful as antiatherosclerotic agents, and are prepared from corresponding carboxylic acids (or their derivatives).

22 Claims, No Drawings

SILICON-BEARING CARBOXYLIC ACIDS AND AMIDES

This invention relates to silicon-bearing amides and methods for their preparation, as well as the use of such amides as pharmaceutical agents, and to pharmaceutical compositions containing such amides, as well as to intermediates in the preparation of such amides.

The silicon-bearing amides involved in this invention are designated as Compounds I, and are conveniently represented by the formula:

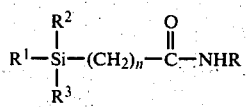

wherein n is a whole integer of from 2 to 20, eg 2, 3 or 4; each of $R^1$, $R^2$ and $R^3$ is, independently, either (a) alkyl having from 1 to 22 carbon atoms, (which may be branched or unbranched); provided that the sum of n and the number of carbon atoms in any one of $R^1$, $R^2$ or $R^3$ is not greater than 34, preferably not greater than 20; or (b) a radical of the formula

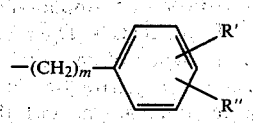

in which m is 0, 1 or 2, and each of R' and R" is independently a hydrogen atom, alkyl having from 1 to 3 carbon atoms, alkoxy having from 1 to 3 carbon atoms, or halo having an atomic weight of from about 19 to 127; and R is of type (a) an aralkyl-type radical of the structure:

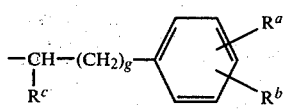

wherein g is 0, 1 or 2;

$R^a$ is a hydrogen atom, halo having an atomic weight of from about 19 to 127, alkoxy having from 1 to 4 carbon atoms, or alkyl having from 1 to 4 carbon atoms, or trifluoromethyl;

$R^b$ is a hydrogen atom, alkyl having from 1 to 3 carbon atoms, alkoxy having from 1 to 3 carbon atoms, or halo having an atomic weight of from about 19 to 36; and $R^c$ is subtype (i) a hydrogen atom;
subtype (ii) a radical of the structure

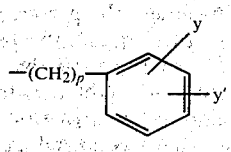

in which p is 0, 1 or 2, and y is a hydrogen atom, halo having an atomic weight of from about 19 to 127, alkoxy having from 1 to 4 carbon atoms, or alkyl having from 1 to 4 carbon atoms; and y' is a hydrogen atom, alkoxy having from 1 to 3 carbon atoms, alkyl having from 1 to 3 carbon atoms, or halo having an atomic weight of from about 19 to 36; or subtype (iii) alkyl having from 1 to 8 carbon atoms; or
R is of type (b) a phenyl-type radical of the structure:

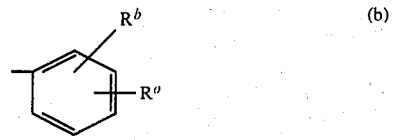

in which $R^b$ is as defined above, and $R^o$ is a hydrogen atom, halo having an atomic weight of from about 19 to 127, ie. alkoxy having from 1 to 4 carbon atoms, or alkyl having from 1 to 4 carbon atoms; or $R^o$ is a radical of the structure $R^f$:

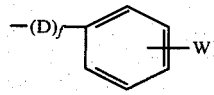

in which D is $-CH_2-$ or $-O-$;
f is 0 or 1; and

W is a hydrogen atom, halo having an atomic weight of from about 19 to 80, alkoxy having from 1 to 3 carbon atoms, or alkyl having from 1 to 3 carbon atoms; or R is of type (c) an indolyl radical of the structure:

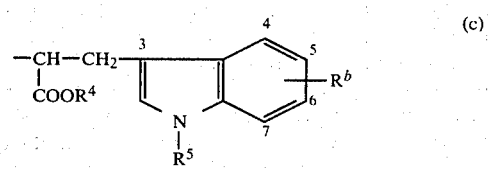

wherein $R^b$ is as defined above;

$R^4$ is alkyl having from 1 to 8 carbon atoms or benzyl (unsubstituted); and $R^5$ is a hydrogen atom, alkyl having from 1 to 8 carbon atoms or benzyl (unsubstituted); or R is (d) a benzocycloalkyl radical of the structure:

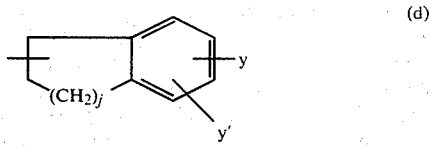

wherein y and y' are as defined above; and
j is a whole integer of from 1 to 4.

In the above-presented definition of Compounds I, halo having an atomic weight of from about 19 to 36, includes fluoro and chloro; halo having an atomic weight of from about 19 to 80 includes fluoro, chloro and bromo; while halo having an atomic weight of from about 19 to 127 includes fluoro, chloro, bromo and iodo. Exemplary of alkyl or alkoxy having from 1 to 3 or 1 to 4 carbon atoms is methyl, or methoxy and ethoxy. Unless otherwise indicated, alkyl and alkoxy may be branched or unbranched.

Compounds I may be viewed as consisting of two major classes, ie Compounds Ia where each of $R^1$, $R^2$ and R$^3$ is alkyl, ie of type (a) and Compounds Ib where at least one of R$^1$, R$^2$ and R$^3$ is of type (b).

It is preferred that for compounds Ia that R$^1$ is unbranched alkyl of 8 to 18 carbon atoms, eg n-decyl, particularly where each of R$^2$ and R$^3$ is alkyl of from 1 to 3 carbon atoms, eg methyl.

Preferred compounds Ib are those in which two of R$^1$, R$^2$ and R$^3$ are the same. For example where R$^1$=R$^2$=type (b) in which m=0 or 1, particularly 0, eg phenyl and R$^3$=type (a) e.g. n-butyl or n-decyl.

Those compounds I in which n is other than 2 are novel and constitute an embodiment of this invention. Particularly preferred are those compounds where n is from 3 to 10, especially 3 to 6.

The particular sub-class of compounds Ia in which n is 2, and each of R$^1$, R$^2$ and R$^3$ is of type (a) ie alkyl, are disclosed and claimed together with methods for their preparation and utility in copending Ser. No. 74,003 (filed Sept. 10, 1979), now abandoned of S. Barcza, and are designated as Compounds Ia'.

The particular sub-class of compounds Ib in which n is 2 and any of R$^1$, R$^2$ and R$^3$ is of type(b) are disclosed and claimed, together with methods for their preparation and utility, in copending application Ser. No. 74,002 (filed Sept. 10, 1979), now abandoned of R. E. Damon II, and are designated as Compounds Ib'.

Further preferred forms of Compounds I when R is of type (a) or (b) and R$^o$ is not R$^f$, are that it is preferred that when R$^a$, R$^o$ or y is other than a hydrogen atom and R$^b$ (or y') is a hydrogen atom, that R$^o$, or R$^a$, or y be located at the 4-position; and that when R$^b$ (or y') is also other than a hydrogen atom that R$^a$ or R$^o$ and R$^b$ (or y and y') are the same, and it is additionally preferred that they be located at the 2- and 4-positions of the phenyl ring. When R is of type (a) where g=1, and R$^c$ is of type (ii) where p=0, then R can be an 1-(phenyl)-2-(p-methylphenyl) ethyl radical, and when R$^c$ is of type (ii) where p=1, then R can be an 1-(benzyl)-2-phenylethyl radical, said radicals being especially preferred.

With particular respect to the substituent R$^o$ when it is a radical R$^f$, it will be appreciated that when D=CH$_2$ and f=1, then the radical R$^f$ is of the benzyl type. When D=oxygen and f=1, then the radical R$^f$ is of the phenoxy-type. When f=zero, then the radical R$^f$ is of the phenyl-type. Hence, when R is of type (b) and R$^o$ is of type R$^f$ where f=zero, then R can be a biphenylyl radical. The radical R$^f$ is preferably at the para-position. When W is other than a hydrogen atom, it is preferably at the para-position.

With respect to R, when it is of type (c), it is preferred that when R$^b$ is other than a hydrogen atom, it be located at the 5-position of the indole nucleus. It is also preferred that when R$^4$ is alkyl, it is unbranched, particularly ethyl.

With respect to R when it is of type (d) it is preferred that when y is other than a hydrogen atom, that it be located at a carbon atom ortho to the ring junction; and that when y' is also other than a hydrogen, it is preferred that it be the same y, and it is additionally preferred that it be in para-relationship to y'. It is additionally preferred that the amide group be linked to a carbon of the cycloalkyl moiety which is directly bonded to a ring junction carbon. It is also preferred that j be 1, ie, that the benzocycloalkyl nucleus be indanyl, and particularly 1-indanyl.

In the above-presented definitions, when R$^o$, R$^1$ or y is halo, it is preferred fluoro or chloro, and particularly chloro; and when R$^2$ or y' is halo it is preferably chloro.

Compounds I of this invention may be obtained by reaction of a primary amine bearing the desired moiety—R as defined above, with a carboxylic acid (or derivative thereof) bearing the "acyl" portion of the desired Compound I. Such acylation may be carried out by conventional means employed in converting a primary amine function to its corresponding secondary amide, such as are reported in the literature. A particularly convenient method of obtaining compounds I is described below.

The compounds of formula (I) may be prepared according to the following reaction scheme (process a):

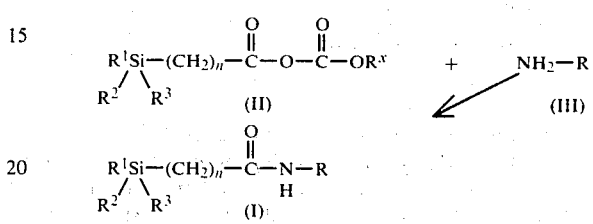

wherein R$^x$ is lower alkyl having 1 to 4 carbon atoms, and R$^1$, R$^2$, R$^3$, n and R are as defined above.

The compounds of formula (I) are prepared by reacting the mixed anhydride of formula (II) with a substituted amine of the formula (III). The reaction is carried out neat or in the presence of an inert organic solvent such as the ethers, halogenated hydrocarbons, e.g., methylene chloride, chloroform and the like, or an excess of a compound of the formula (III), preferably methylene chloride. The temperature of the reaction is not critical, but it is preferred that the reaction be run from about −50° to +30° C., preferably from about −10° to +20° C.

The compounds of formula (II) are prepared according to the following reaction scheme (process b):

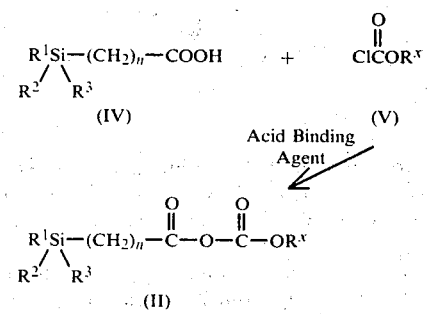

wherein R$^x$, R$^1$, R$^2$, R$^3$ and n are as defined above.

The compounds of formula (II) are prepared by reacting a compound of the formula (IV) with an alkylchloroformate of the formula (V) in the presence of an acid binding agent. Although the particular acid binding agent employed is not critical, the preferred acid binding agents include pyridine, triethylamine, diisopropylamine and the like, preferably triethylamine. It is preferred that the reaction be carried out in the presence of aprotic solvents such as the halogenated hydrocarbons, e.g., methylene chloride, chloroform and the like, the aromatic hydrocarbons, e.g., benzene, toluene and the like, acetonitrile, preferably methylene chloride. The temperature of the reaction is not critical, but it is preferred that the reaction be run from about −50° to +30° C., preferably from about −20° to +20° C.

The product may be recovered by conventional techniques, however, in the instant case, compounds of the formula (II) are not isolated but used in situ in the preparation of the final compounds. In place of mixed anhydride (II) other well-known activated carboxylic acid derivatives may be used, e.g., acyl halides, active esters or carbodimide adduct.

Another convenient method of preparing compounds I comprises reacting (process a2) an acyl halide of the formula II'

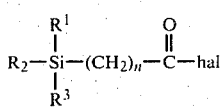

in which $R^1$, $R^2$, $R^3$ and n are as defined above, and hal is either chloro or bromo (preferably chloro) with a compound III (as defined above), in the presence of an acid binding agent, in an inert medium at moderate temperatures, eg from about 10° to 50° C. preferably at about 20° to 30° C. Acid binding agents are the same as described with respect to process (a), above, triethylamine being preferred.

The acyl halides II' may be prepared in the conventional manner, eg by treating (process b2) a corresponding compound IV, with a halogenating agent capable of contributing a chlorine or bromine atom, eg thionyl chloride (or-bromide, as appropriate). Dimethylformamide may be included as a catalyst.

In the above-described processes (a2 and b2) neither the media nor the temperature are critical to the reactions, and where the reactants or reagents are liquid, an excess thereof may serve as the reaction medium.

The compounds of formula (IV) may be prepared according to the following reaction scheme (process c):

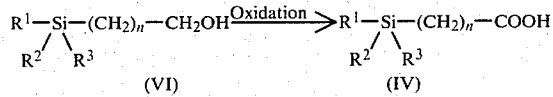

wherein $R^1$, $R^2$, $R^3$ and n are as defined above.

The compounds of formula (IV) are prepared by reacting a compound of the formula (VI) with an oxidizing agent such as chromium trioxide, potassium permanganate, and the like; for example, chromium trioxide under acidic conditions in the presence of acetone and a small amount of water. Although the particular acid employed is not critical, the preferred acids include the acids such as phosphoric acid, acetic acid or sulfuric acid, the latter being especially preferred. The particular solvent employed is preferably acetone, or acetone in combination with water, although the combination of water and other inert solvents could also be employed such as diethylether. The temperature of the reaction is not critical, but it is peferred that the reaction be run from about −40° to +30° C., preferably from about −10° to +5° C. Methods for preparing those compounds VI that are known may be adapted to prepare those compounds VI which are novel, eg U.S. Pat. No. 3,585,228.

The preparation of Compounds IV in which each of $R^1$, $R^2$ and $R^3$ is alkyl and n is 2, ie Compounds IVa, is disclosed in above-mentioned application Ser. No. 74,003, (from corresponding Compounds VI). Those compounds IV where $R^1$, $R^2$ and $R^3$ are each methyl when n is 5 or less; as well as compounds IV, in which one or more of $R^1$, $R^2$ and $R^3$ is phenyl and the remainder methyl, when n is 2, are known in the literature, eg JACS 76, 1609, ie compounds IVb. Compounds IV, other than Compounds IVa and IVb are novel and constitute an embodiment of this invention, ie compounds IVc. Additional embodiments of this invention are novel methods of preparing compounds IVc, which methods can also be employed to prepare compounds IV in general. Compounds IVc may be prepared by the general method for preparing compounds IV*described above as process (c).

*The method disclosed in the above-mentioned article (JACS 76, 1609), may be adapted for the preparation of Compounds IV in general, besides those compounds IVb, disclosed therein.

A convenient method for preparing compounds IV, in general, comprises preparing a corresponding malonic acid ester, which is then subjected to hydrolysis/-decarboxylation to obtain the desired Compound IV (process d). The general method of preparing the malonic acid esters is disclosed in the literature; such a method, being described in the preparation of certain compounds IVb in JACS 76, 1609, as mentioned above.

Process (d) may be conveniently represented by Reaction Scheme D below, in which $R^S$ is the moiety

in which, R, $R^2$ and $R^3$ are as defined above; $R^5$ is lower alkyl, eg having from 1 to 4 carbons, eg methyl or ethyl; L is a leaving group ie a residue of a strong acid, such as halo having an atomic weight of from about 34 to 127, ie chloro, bromo or iodo, or a sulfonate and the like; and $M^1$ is an equivalent of an active metal, and $M^2$ is an equivalent of a cation of a strong base such as an alkali or alkali earth metal, preferably potassium. Sulfonate radicals suitable as L—include the alkanesulfonates, eg the alkyl portion having from 1 to 8 carbon atoms, such as methanesulfonate, and arylsulfonates, eg having a substituted or unsubstituted phenyl, such as p-toluenesulfonate.

It is a preferred embodiment of this invention to condense as many steps as possible in this process, for example to prepare intermediates (or reactants) in situ, eg VII and VIII, so that the need to recover such is avoided, and the reaction medium for one step can be utilized for the next one, and that the same vessel or apparatus can serve for as many steps as possible. Thus, in a preferred form of process (c) compound VIII is prepared in situ (or obtained per se from another source); Compound VII is prepared in the same vessel in situ, and VII and VIII reacted to form IX which is then de-esterified-decarboxylated in the same vessel, and the reaction product (IV) recovered.

Reaction Scheme D

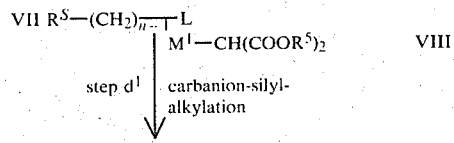

-continued

Reaction Scheme D

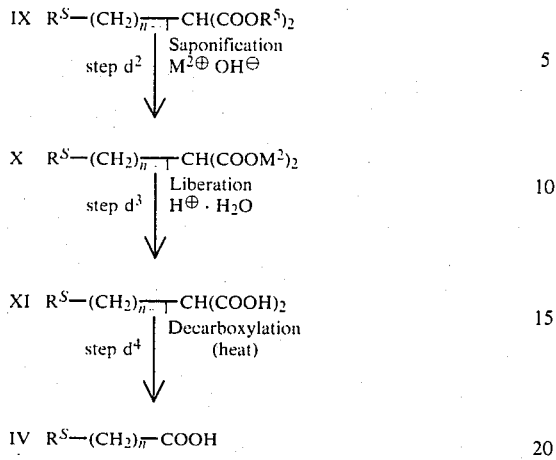

It will be appreciated that reaction Scheme D is an outlined representation, since in actual practice some steps can overlap or go by intermediates which are not shown. Saponification and liberation steps can be carried out in the conventional manner. The decarboxylation step (d⁴) is conveniently carried out by heating, typically at from about 60° to 200° C. It is particularly convenient to carry out the decarboxylation under reduced pressure.

In preparing Intermediates IX (by process d¹) a leaving group-bearing-silyl-reactant, (VII), is reacted with an metallo-carboxylic ester compound, ie a compound VIII, eg sodio-methyl malonate, under conditions conventionally employed in carrying out Grignard-type reactions, ie under essentially anhydrous conditions and employing an inert organic reaction medium. Moderate temperatures are employed, eg from about 10° to 80° C., particularly from about 45° to 65° C. Suitable reaction media include dimethyl formamide, polyethers and cyclic ethers such as tetrahydrofuran. M¹ may be an alkaline metal, such as lithium, potassium or sodium, preferably sodium, or a magnesium halide, such as —MgCl or MgBr. Compounds VIII may be prepared in the conventional manner for converting a malonic acid ester to its metallo-form. They are conveniently prepared by reaction of an active metal source, eg an alkali metal hydride, such as NaH, alkoxide or alkylate, with a corresponding malonic acid ester, in inert media, under conditions conventionally employed in preparing metallo-organic reagents, eg under essentially anhydrous conditions, and at a temperature of from about 0° to 15° C. It is particularly convenient to prepare a Compound VIII and use it in situ, since the reaction media and reaction conditions for the preparation thereof can also serve for process (d¹). It is to be understood that the term inert with respect to media, includes those which are not strictly inert, but are not detrimental, such as the alcohol/alkoxides systems.

Alternatively, a Compound IV may be prepared by hydrolysis of its corresponding nitrile (XII). Compounds XII may be obtained in a manner generally paralleling that presented above as process (d), except that intermediate compounds are employed in which a nitrile radical replaces a carboxylic ester radical. This alternative method (process d') is conveniently represented by Reaction Scheme D', below in which the definitions are as given in connection with process (d).

Reaction Scheme D'

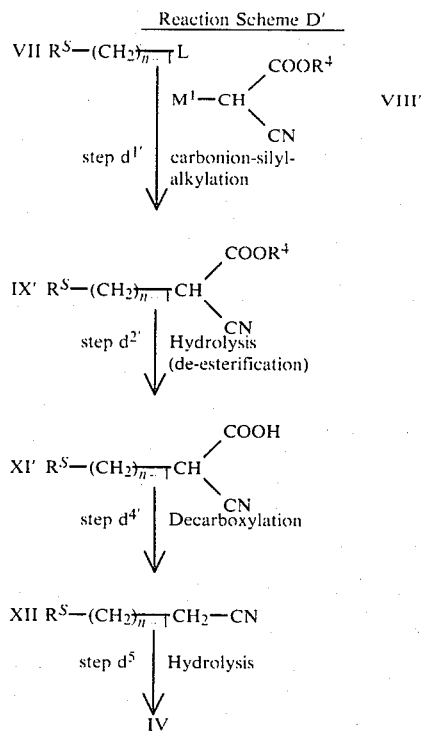

Again, it will be appreciated the reaction scheme is in outline form, but is useful in illustrating the general course of the reaction and major intermediates. The individual reaction steps are carried out in the same manner as the corresponding steps of process (d). It is particularly convenient to carry out Step d2' in the presence of a relatively large amount of acetic acid with heating at decarboxylating temperatures, so that Step 3' can be accomplished concurrently, to obtain the resulting compound XII directly. The hydrolysis Step (d⁵) may be accomplished in the conventional manner for hydrolyzing a nitrile to its corresponding acid. Step (d⁵) is conveniently accomplished in two phases, ie the nitrile (XII) is hydrolyzed in a basic aqueous medium, such as aqueous potassium hydroxide with a co-solvent, eg a lower alcohol, to form the corresponding salt of the acid, (IV) and then neutralized (with acid) to free the corresponding acid (IV). In Step (d2'), if appreciable hydrolysis of the nitrile group (of IX') occurs, a co-product would be a malonic acid derivative, which would then be decarboxylated as in Step (d⁴) of process (d) with no disadvantage as the same product IV, would result, as if process (d') were followed throughout.

In addition, those compound IV in which n is from 2 to 9, ie compounds IVe may be obtained by a procedure (process e) involving a cyclic silyl ether of the formula

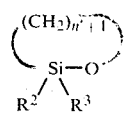
XIII in which R² and R³ are as defined above, preferably having from 1 to 6 carbon atoms, n' is a whole integer of from 2 to 9, especially 2 to 4, to yield a corresponding alcohol, compound VIe which is then oxidized to the corresponding compound IVe which procedure is conveniently represented by Reaction Scheme E below in which $R^1$, $R^2$ and $R^3$ are as defined above; n' is a whole integer of from 2 to 9 and $M^3$ is an equivalent of an active metal radical, eg an alkali metal, or a magnesium halide, ie MgCl, MgBr or MgI. Those compounds VI are preferred in which the sum of the carbon atoms of the longest alkyl radical (as represented by any of $R^1$, $R^2$ or $R^3$) plus n is greater than 5 and particularly greater than 7 and especially greater than 11.

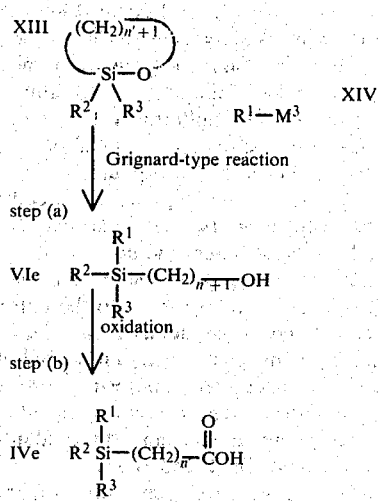

The oxidation (step b) of process (e) may be carried out in the same manner as that in process (c) described above. Step (a) is a Grignard-type reaction, and is carried out under conditions conventionally employed in such reactions. Reaction temperatures are not critical and are moderate, eg 10° to 100° C. Typically the reactants are mixed at a lower temperature eg 0° to 60°, and the resulting mixture then allowed to rise to the preferred temperature for the reaction eg, from about 20° to the reflux temperature of the solvent. It is convenient to form a reagent XIV in the conventional manner of preparing a Grignard-type reagent, ie under anhydrous conditions in an inert organic medium, eg dry THF, and use it in situ, since the same type of media and conditions are employed in Step (a).

Recovery of the intermediates and products obtained by the above-described procedures may be effected by conventional techniques, such as crystallization, precipitation, vacuum distillation, and chromatographic techniques such as column or thin layer chromatography and the like.

It will be understood that many compounds of this invention, eg compounds I, may exist in the form of stereoisomers, eg optically active isomers, ie enantiomers, which can be prepared from respective stereoisomers, eg optically active compounds III or separated and recovered by conventional techniques, eg, resolution and such isomeric forms are also included within the scope of this invention.

Many of the reagents and compounds involved in the above-described procedures are known, eg compounds III, V, VII, XIII and XIV and precursors of VIII and VIII' and may be obtained commercially or may be prepared by methods described in the literature, while those compounds not specifically described in the literature may be prepared by analogous methods from known starting materials.

STATEMENT OF UTILITY

The compounds of formula I of this invention are useful as pharmaceutical agents in animals. In particular, the compounds of the formula I are useful in controlling the cholesterol ester content of mammalian arterial walls and are therefore particularly indicated for use as anti-atherosclerotic agents, ie. agents useful in the prophylactic treatment of atherosclerosis and in the controlling of atherosclerotic conditions due to cholesterol ester accumulation in the arterial walls. Such ability of the compounds of the formula I is indicated by known test procedures in which the total cholesterol ester content of cultured cells is shown to be reduced by a test compound, as compared to untreated cells, and carried out, for example, by the following procedures:

(A) Cell culture

Rhesus monkey smooth muscle cells (from the arterial, eg. aorta, wall) obtained by the method of K. Fisher-Dzoga et al (Experimental and Molecular Pathology 18, 162–176 (1973)) are routinely grown in 75 cm² tissue culture flasks using Minimum Essential Medium (Eagle) supplemented with 10% fetal bovine serum. For testing a 75 cm² flask with a near confluent cell growth is selected. The cells are removed from the flask surface by mild enzymatic treatment with pronase. After centrifugation and decanting the enzyme solution, the cell pellet is resuspended in an appropriate volume of media for seeding the desired number of 60 mm tissue culture dishes. Five (5) ml of the diluted cell suspension are pipetted into each dish. After seeding, the dishes are labelled with the cell type, date and flask number of origin and incubated at 37° C. in approximately 5% $CO_2$ atmosphere in a high humidity incubator. When the cultures are confluent, the actual drug testing is begun. Test compounds are routinely solubilized in 100% ethanol. An equivalent amount of ethanol is added to control groups as well. The tissue culture dishes are randomly divided into groups. To one group, hyperlipemic rabbit serum (HRS) is added at 5% by volume (control). To the remaining groups, 5% HRS and 1 mg per 100 ml of media of the test compound are added. The dishes are returned to the incubator for an additional 24 hours. All operations through to the final incubation are performed using sterile technique in a laminar flow hood. After the incubation period, the dishes are microscopically observed with the Zeiss Axiomat with phase contrast optics and the conditions of the cultures are recorded; especially in regard to the size, number and configuration of cytoplasmic inclusions and to cellular morphology. The media is removed from the cultures and 0.9% sodium chloride solution is added. The cells are removed from the flasks with the aid of a rubber policeman and transferred to a conical graduated centrifuge tube. The cells are washed three times by suspending in an isotonic salt solution, centrifuging at 800×g for 10 minutes and aspirating the supernatant fluid.

(B) Cell extraction procedure

An appropriate volume of isopropyl alcohol (about 1 ml/mg protein) is then added to the cell pellet and the sample sonicated with a micro probe (140×3 mm) for 10 seconds with a "LO" setting of 50 on a Bronwell Biosonik IV. After centrifugation for 15 minutes at 80033 g, the clear supernatant is decanted and an aliquot taken for cholesterol analysis.

The residue is dissolved in 0.1 N sodium hydroxide and an aliquot taken for protein determination by the method of Lowry, et al. (J. Biol. Chem. 193, 265; 1951).

(C) Assay

Free cholesterol: The isopropyl alcoholic solutions of standards, samples and blank (isopropyl alcohol alone) are treated in a similar manner. An aliquot of 0.4 ml of free reagent (Reagent A, Table 1 below) is added to a 10×75 mm disposable glass test tube to which 20 μl of the isopropyl alcoholic solution is added and mixed. After standing at room temperature for approximately 5 minutes, 0.8 ml of 0.5 N sodium hydroxide (Reagent C, Table 1) is added and mixed. The fluorescence is measured with an Aminco-Bowman spectrophotofluorometer with an excitation wavelength of 325 nm and emission wavelength of 415 nm. A 1 cm light path cuvette is used with a xenon lamp, an IP28 photomultiplier tube and 2 mm slits.

Total cholesterol: The same procedure described above for free cholesterol is followed for total cholesterol except that the total reagent (Reagent B, Table 1) is used instead of the free reagent and the samples are incubated for 20 minutes at 37° C. before the addition of the 0.5 N sodium hydroxide solution (Reagent C, Table 1).

Alternatively, the assay for cholesterol, ie Step C (above) obtained from Steps A and B, may be carried out by the method of Ishikawa et al (J. Lipid Res. 15, 286; 1974).

The amount of cholesterol ester is found by subtracting the amount of free cholesterol from the total cholesterol content of the cells determined by the assay. A finding of a lower amount of cholesterol ester in the group of cells to which test compound was added, as compared to the control group (untreated) shows that the test compound is active in reducing the cholesterol ester in the cells.

TABLE 1

| Composition of Reagents for Cholesterol Determination | | |
|---|---|---|
| A. Free Cholesterol Reagent | | |
| Sodium phosphate buffer pH 7.0 | .05 | M |
| Cholesterol oxidase | .08 | U/ml |
| Horseradish peroxidase | 30. | U/ml |
| p-Hydroxyphenylacetic acid | .15 | mg/ml |
| B. Total Cholesterol Reagent | | |
| Sodium phosphate buffer pH 7.0 | .05 | M |
| Cholesterol ester hydrolase | .08 | U/ml |
| Cholesterol oxidase | .08 | U/ml |
| Horseradish peroxidase | 30. | U/ml |
| Sodium taurocholate | 5. | mM |
| Carbowax-6000 | .17 | mM |
| p-Hydroxphenylacetic acid | .15 | mg/ml |
| C. Sodium Hydroxide Solution | .5N | |

When the compounds are employed for the above utility, they may be combined with one or more pharmaceutically acceptable carriers, e.g., solvents, diluents and the like, and may be administered orally in such forms as tablets, capsules, dispersible powders, granules, suspensions containing, for example, from about 0.5 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.5 to 5% suspending agent in an isotonic medium. These pharmaceutical preparations may contain, for example, from about 0.5% up to about 90% of the active ingredient in combination with the carrier, more usually between 5% and 60% by weight.

The antiatherosclerotic effective dosage of active ingredient employed for the reduction of cholesterol ester content in the arterial walls of a mammal may vary depending on the particular compound employed, the mode of administration and the severity of the condition being treated. However, in general, satisfactory results are obtained when the compounds of formula I are administered at a daily dosage of from about 0.2 milligrams to about 500 milligrams per kilogram of animal body weight, preferably given in divided doses two to four times a day, or in sustained release form. For most large mammals, the total dialy dosage is from about 10 milligrams to about 5,000 milligrams preferably from about 10 milligrams to 2,000 milligrams. Dosage forms suitable for internal use comprise from about 2.5 to 2,500 milligrams of the active compound in intimate admixture with a solid or liquid pharmaceutically acceptable carrier. Solid carriers include starch, lactose and kaolin, while liquid carriers include sterile water, polyethylene glycols and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants eg vitamin E, ascorbic acid, BHT and BHA.

The preferred pharmaceutical compositions from the stand-point of ease of preparation and administration are solid compositions, particularly tablets and hard-filled or liquid-filled capsules.

A representative formulation for administration orally three times a day prior to feeding in the treatment of atherosclerosis is a gelatin capsule prepared by conventional techniques to contain the following

| Ingredient | Weight (in Mg.) |
|---|---|
| D.L-5,5-dimethyl-5-sila-n pentadecanoyl-1'-phenyl-2'-p-tolyl-ethylamide (of Example 5) | 250 |
| corn oil | 250 |

As is the present understanding in the art, controlling the total cholesterol content of an arterial wall by inhibiting the accumulation thereof by reducing the cholesterol ester content thereof, advantageously inhibits the formation of plaques in the arterial wall.

The following examples of the preparation of intermediates and final compounds of the invention are illustrative of the invention. All temperatures are centigrade (°C.) and room temperature is 20° to 30° C. unless indicated otherwise.

Where "dry" or absolute solvents are employed, they are freshly distilled from a metallo-hydride, eg $CaH_2$ for dimethylformamide, and lithium aluminum hydride for tetrahydrofuran (THF), or as specified, eg through molecular sieves. Where temperatures are given for distillations in a Kugelrohr apparatus, the temperatures are for the heating unit (pot) not the condensation column. Temperatures for fractional distillations, eg in a Vigreux column, are internal temperatures (boiling points). When it is mentioned that an operation is carried out "under nitrogen", it is understood that the operation is being carried out under essentially anhydrous conditions, in an atmosphere of dry nitrogen gas (so as to essentially exclude moisture and oxygen). "Drying" of any organic extract is done over anhydrous sodium sulfate and the solids filtered off to obtain a filtrate containing the desired product. Concentrations are done by evaporation under vacuum, typically a "low" vacuum, eg at about 15–40 mm Hg.

EXAMPLE 1

This example illustrates the preparation of a compound Ia, employing a compound IVa', obtained via process (d).

6,6-Dimethyl-6-sila-n-hexadecanoyl-1'-benzyl-2'-phenylethylamide

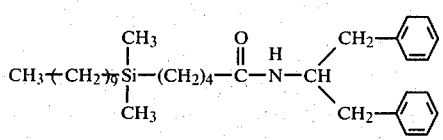

Step A, n-decyl-dimethyl-(3-chloropropyl)-silane

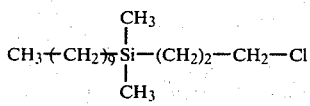

Under nitrogen 32.4 g (147 mmole) of n-decyl bromide is added to 3.8 g (156 m atom) of magnesium turnings, in 100 ml. of absolute tetrahydrofuran (THF) cautiously (over a period of about 0.5 hr.) with external cooling (cold water bath) as needed to maintain a temperature of below 38°. The resulting mixture is then refluxed for 10 min, (to produce a Grignard reagent) then cooled to 35°. The Grignard reaction mixture is then added to 27.3 g (159 mmole) of (3-chloropropyl)-dimethyl-chlorosilane in 100 ml of absolute tetrahydrofuran, with temperatures maintained at below 15° (using a salt-ice bath). The mixture is then stirred at room temperature for 2 days then heated at near reflux for 1 hr. The mixture is then cooled, poured into ice-water and the organic material extracted with methylene chloride. The extract is dried, and concentrated to obtain the crude product of this step as oily residue. The residue is distilled using a Vigreux column, to obtain refined product of this step as a main fraction recovered at 118°–125° at 0.150 mm Hg. for use in the next step (B).

Step B, n-Decyl-dimethyl-(3-iodopropyl)-silane

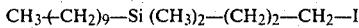

A mixture of 25.0 g (166 mmoles) of sodium iodide, 120 ml. of acetonitrile (dried over molecular sieves) and 26.4 g (95.4 mmoles) of n-decyl-dimethyl (3-chloropropyl)-silane is stirred at near the reflux temperature of the mixture (at about 80°) for 40 hrs. After cooling, the mixture is mixed with water and toluene, and the organic phase recovered, washed thrice with water, then dried and concentrated (to about 40 ml) of an oil which on distillation using a Kugelrohr apparatus yields as the main fraction, refined title product of this step at 83° to 139°, at 0.140–0.095 mm Hg. for use in the next step.

Step C, Methyl-2-methoxycarbonyl-6,6-dimethyl-6-sila-n-hexadecanoate

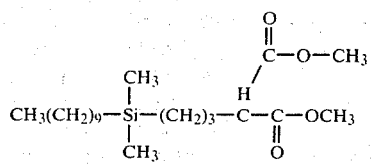

To a reaction vessel system filled with nitrogen, 964 mg (24.5 mmole) of 61.1% sodium hydride in mineral oil is added, which is washed free of the oil by employing 3 portions of petroleum ether/hexane (1:1). The thus-washed sodium hydride is then suspended in 20 ml of fresh hexane and added in several portions to 8.1 g (22.0 mmoles) of n-decyl-dimethyl-(3-iodopropyl)-silane plus 3.6 g (27.3 mmole) of dimethyl malonate in 25 ml of dry dimethylformamide plus 25 ml of dry petroleum ether, with stirring and cooling at such a rate that hydrogen gas evolution is controlled, and the temperature is at 0° to 10° (new solids form). The reaction mixture is then stirred in a bath at 55° for 2 hrs. and then at 65° for 1 hr. After cooling to room temperature, 2 ml of acetic acid (85%) is added, followed by an excess of water and petroleum ether. The organic layer is separated, washed thrice with water, dried and then concentrated to obtain the crude title product of this step as an oily residue, which is distilled through a Vigreux column to obtain refined title product of this step at 135°–139° at 0.105 mm Hg.

Step D, 6,6-dimethyl-6-sila-n-hexadecanoic acid

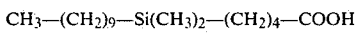

A mixture of 6.7 g (18 mmole) of methyl-2-methoxycarbonyl-6,6-dimethyl-6-sila-n-hexadecanoate (from step C) in 50 ml of methanol and 3.0 g (about 48 mmole) of potassium hydroxide (powder) in 50 ml of methanol is refluxed for 45 min. The resulting mixture is then concentrated to a solid. Dilute hydrochloric acid (2N) is then added to the solid (in excess, to acid pH) and the mixture extracted with methylene chloride. The extract is dried, then concentrated to a residue. The residue is heated to 160°–170° under reduced pressure (approx. 15 mm Hg), for 1 hour, then distilled under high vacuum through a jacketed Vigreux column to obtain refined title product of this step (as the main fraction) at 145°–140° at 0.101–0.090 mm Hg.

Step E, 6,6-dimethyl-6-sila-n-hexadecanoyl-1'-benzyl-2'-phenyl-ethylamine 3.0 g (12.1 mmol) of the hydrochloride salt of N-benzyl-2-phenyl-ethylamine is distributed between dilute aqueous sodium hydroxide and methylene chloride. The organic phase (containing the free amine) is dried, then concentrated in vacuo and redissolved in 25 ml of dry methylene chloride and held for reaction with the acyl chloride, below.

0.025 ml of N,N-dimethylformamide is added to 1.6 g (5.32 mmol) of 6,6-dimethyl-6-sila-n-hexadecanoic acid in 50 ml of dry methylene chloride/toluene (1:1 v/v) and the resulting solution cooled (in an ice bath), and 1.5 ml (20.9 mmole) of thionyl chloride added (with stirring). Stirring is continued for 0.5 hr. at 0° to 20°, then the mixture concentrated in vacuo to an oily residue (which is the acyl chloride), which is then dissolved in 25 ml of dry methylene chloride and cooled (with ice-water). The amine-containing solution is then mixed with the cold acyl chloride-containing solution. The resulting mixture (a slurry results) is stirred for 16 hr. at 20°, then the solvent removed by evaporation in vacuo, to obtain a residue, which is distributed between hexane and an excess of dilute hydrochloric acid. The organic phase is separated, then washed with two portions of dilute hydrochloride acid, then with three portions of dilute aq. sodium hydroxide, followed by one wash with sat. aq. sodium bicarbonate. The organic phase is then dried, and concentrated to an oily residue (crude product) which is then quick-chromatographed on silica-gel, eluting with methylene chloride containing increasing concentrations of methanol. The title product is recovered as the main fraction (using 2% methanol) and obtained as a residue by heating in a rotating flask at 110° at 0.1 mm Hg. to remove solvent (eluant).

EXAMPLE 2

D,L-6,6-Dimethyl-6-sila-n-hexadecanoyl-1'-phenyl-2'-p-tolyl-ethylamide

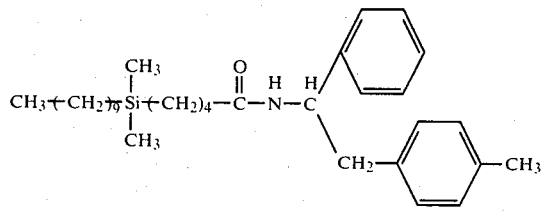

Step A, 6,6-dimethyl-6-sila-n-hexadecanoyl chloride

A 25 ml. solution of dry methylene chloride solution of the title acyl chloride of this step is prepared from 1.6 g of 6,6-dimethyl-6-sila-n-hexadecanoic acid as in Step E of Example 1.

Step B, D,L-6,6-Dimethyl-6-sila-n-hexadecanoyl-1'-phenyl-2'-p-tolyl-ethylamide

To the acyl chloride solution of Step A, is added a mixture of 1.0 ml (7.19 mmol) of triethylamine and 1.1 g (5.21 mmol) of D,L-1-phenyl-2-p-tolyl-ethylamine and 25 ml of dry methylene chloride, with ice cooling. The resulting mixture is stirred at 20° for 17 hr., concentrated, and the residue distributed between hexane and dilute hydrochloric acid. The organic phase is separated, then washed twice with dilute hydrochloric acid and thrice with dilute aq. sodium hydroxide, and then once with saturated aq. sodium bicarbonate, then dried and concentrated to obtain the crude title product as a residue. The residue is quick-chromatographed on silica gel, eluting with methylene chloride and gradually increasing concentrations of methanol; the refined title product being recovered from the fraction obtained with 1.5% methanol, yield a crystalline solid, m.p. (42)-43-45°.

EXAMPLE 3

5,5-dimethyl-5-sila-n-pentadecanoic acid

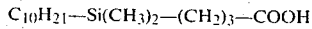

This example illustrates the preparation of intermediate compounds IV and VII, via process (e).

Step A, 5,5-dimethyl-5-sila-n-pentadecanol

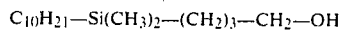

A Grignard reagent is prepared by adding, under nitrogen, 50 g (226 mmol) of n-decyl bromide to 6.5 g (268 mmol) of magnesium turnings in 200 ml of absolute THF at 20°-40°. After heating at 55°, 28.1 g (215 mmol) of 1,1-dimethyl-1-sila-2-oxacyclohexane is added to the Grignard-reagent, and the mixture stirred for 20 hr., at 60°. After cooling, the reaction mixture is poured into a mixture of saturated aq. ammonium chloride, ice and hexane. The organic phase is recovered and washed with water, then dried, and concentrated to the crude title product of this step (colorless), which is refined by distilling through a Vigreux column at 116°-113°, at 0.190-0.175 mm Hg.

Step B, 5,5-dimethyl-5-sila-n-pentadecanoic acid

To a solution of 25.0 g (91.7 mmol; 366.8 electron equivalents) of 5,5-dimethyl-5-sila-n-pentadecanol in 100 ml of pyridine, is added 21.5 g (136 mmol; 408 electron equivalents) of potassium permanganate in 320 ml of pyridine, at 20°-25° with stirring, and stirring is continued for 30 hr. A dark brown precipitate forms which is filtered off (leaving a colorless filtrate). The filter cake is thoroughly washed with methanol and ligroine. The washes and filtrate are combined and concentrated to near dryness. The residue is added to a mixture of water, ice, petroleum ether and dilute hydrochloric acid and the organic phase recovered. The aqueous phase is washed once with petroleum ether, which wash is then combined with the previously recovered organic phase, and the combined organic phases washed thrice with water, dried, and then concentrated to obtain crude title product, which is refined by distillation through a Vigreux column, b.p. 142°-132° at 0.145-0.115 mm Hg.

EXAMPLE 4

5,5-dimethyl-5-sila-n-pentadecanoyl-1'-benzyl-2'-phenyl ethylamine

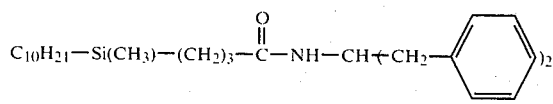

5.3 ml (38.5 mmol) of triethylamine and 5 ml of dry methylene chloride are added to 3.0 g (10.5 mmol) of 5,5-dimethyl-5-sila-n-pentadecanoic acid. The mixture is cooled in an ice/water bath. 1.3 ml (12.3 mmol) of ethyl chloroformate is added with stirring to the cooled mixture (over a period of 5 minutes while the temperature is maintained at from about 0° to 10° by application of a salt/ice bath, as needed. Stirring is continued for 10 min (with salt/ice bath cooling), then 2.6 g (10.5 mmol) of the hydrochloride of 1-benzyl-2-phenyl-ethyl amine suspended in 40 ml of dry methylene chloride, is added at from about 0° to 10°. The resulting mixture is stirred for 3 days at 25°, then poured on ice. The organic phase is separated, dried, and concentrated to yield crude title product as a residue. The product is refined by chromatographing on silica gel with 2% methanol in methylenechloride, then re-chromatographed with methylene chloride-5% ethyl acetate (TLC shows single spot). The product is then further purified by distillation in a Kugelrohr apparatus at 197°–214° at 0.1 mm Hg.

EXAMPLE 5

D,L-5,5-Dimethyl-5-sila-pentadecanoyl-1'-phenyl-2-tolyl-ethylamide (D,L)

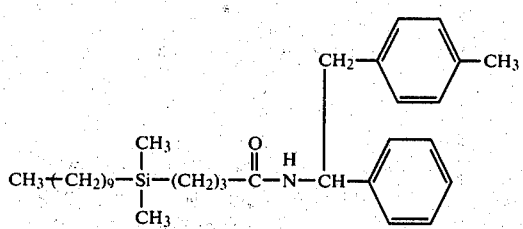

Repeating the procedure of Example 4, but using 2.2 g of D,L-1-phenyl-2-p-tolyl-ethylamine in place of the hydrochloride of the 2.6 g 1-benzyl-2-phenyl-ethylamine used in Example 4, the title product of this example is obtained, refined by distillation in a Kugelrohr apparatus at 202° to 237° at 0.115 to 0.110 mm Hg.

EXAMPLE 6

4-Sila-4,4-dimethyl-n-tetradecanoic acid

Step A, Dimethyl-n-Decyldimethylsilylmethyl malonate

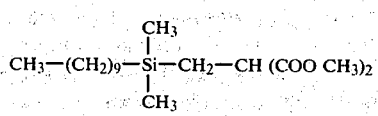

Under anhydrous conditions, 973 mg (24.8 mmoles) of sodium hydride dispersion in mineral oil (61.1% NaH) is washed free of the oil by washing thrice with portions of hexane. The thus-washed sodium hydride is then slurried in 20 ml of hexane and the mixture added under a nitrogen atmosphere, (over a period of 35 minutes) to a solution of 3.27 g (24.7 mmoles) of dimethylmalonate and 8.43 g (24.7 mmoles) of n-decyldimethyl-iodomethylsilane in 20 ml of dry dimethylformamide at from 0° to 8°, with stirring (using a paddle stirrer). Caution is exercized as hydrogen gas evolves during the addition, and a solid forms. Stirring is continued for 1.5 hr. at 55° and then for 1.5 hr. at 63°. The reaction mixture is then cooled to room temperature and acetic acid (85%) is added to obtain a pH of 5. Water, ice and petroleum ether are added, and the organic phase recovered and washed twice with water, then dried, and concentrated to obtain crude product of this step, which is then refined by distilling through a Vigreux column, the product being recovered at 115° to 126°, at 0.097 to 0.100 mm Hg.

Step B, 4-Sila-4,4-dimethyl-tetradecanoic acid

A suspension of 6 g of potassium carbonate in 200 ml of 95% ethanol containing 3.4 g of dimethyl-n-decyl-dimethylsilylmethyl malonate (from Step A) is refluxed for 72 hrs. while stirred (magnetically). The solvent is then removed in vacuo, and the residue taken up in water, acidified with 2N hydrochloric acid and extracted with methylene chloride. The extract is then dried and concentrated to obtain an oily residue. The oily residue is held at 150° and 16 mm Hg pressure for 45 minutes, then distilled under high vacuum; fractions being recovered at from 112° to 147° at from 0.16 to 0.17 mm Hg. TLC indicates that the fractions are not completely converted.

The fractions are combined, dissolved in 50 ml of methanol and added to a solution of 1.5 g of (powdered) potassium hydroxide in 50 ml of methanol, and the mixture refluxed for 24 hrs., then cooled and concentrated by evaporation to a reduced volume. Water-diluted 2N hydrochloric acid is added to the residue giving an acidic pH, and the mixture is extracted with methylene chloride. The organic phase is dried and concentrated to a residue. The residue is then distilled in a Kugelrohr apparatus and refined title product obtained at 153° to 163° at 0.100 to 0.095 mm Hg.

The procedure of this Step (B) is repeated, but the potassium carbonate is replaced with an equivalent amount of potassium hydroxide, simplifying the procedure and giving a higher conversion to the desired product.

Repeating the procedure of this step A, but using in place of the n-decyl-dimethyl-iodomethylsilane, an approximately equivalent amount of:

(a) n-decyl-dimethyl-(4-iodobutyl) -silane:
(b) n-decyl-di-(n-hexyl)-(2-iodoethyl) -silane:
(c) n-octyl-dimethyl-(4-bromo-butyl) -silane:
(d) n-butyl-di-(n-propyl)-(8-bromo-octyl) silane; or
(e) benzyl-dimethyl-(3-iodo-propyl) -silane;

there is accordingly obtained:

(a) dimethyl 4-(n-decyl-dimethyl-silyl) -butyl malonate;
(b) dimethyl 2-(n-decyl-di-(n-hexyl)-silyl) -ethyl malonate;
(c) dimethyl 4-(n-octyl-dimethyl-silyl) -butyl malonate;
(d) dimethyl 8-(n-butyl-di-(n-propyl)-silyl) -octyl malonate; and
(e) dimethyl 3-(benzyl-dimethyl-silyl-propyl malonate.

EXAMPLE 7

6,6-Dimethyl-6-sila-n-hexadecanoic acid

In this example a well sealed 4-necked vessel equipped with a thermometer, a paddle stirrer, dropping funnel, rubber septum, and a distillation head with reflux condenser and Dean-Stark trap, a vacuum and dry nitrogen gas supply is employed, and all steps are carried out in the same vessel.

Step A, n-decyl-dimethyl-(3-chloropropyl)-silane

To a vessel, containing 3.5 g (144 m atom) of magnesium turnings, under nitrogen in 150 ml of absolute THF is added gradually 31.8 g (144 mmol) of n-decyl bromide with stirring (over a period of about 0.5 hr) with cooling to maintain the temperature at between 20° and 38° as slight exotherm and darkening of the mixture occurs (indicating formation of the Grignard reagent). After the addition, the mixture is then heated to reflux for 10 min., then cooled to −10° (some magnesium remains).

At between −10° and 0°, 35.3 g (144 mmol) of 3-chloropropyldimethyl-chlorosilane is added, and the mixture stirred at 20° for 16 hr. (at which time no magnesium remains). The mixture is then refluxed for 1 hr. and then cooled to −10° to 0° (some separation of solids occurs).

Step B, methyl-2-methoxycarbonyl-4,4-dimethyl-4-sila-n-tetradecanoate

To the cooled reaction mixture of Step A, is added at −10° to 0°, 250 ml of dry 2-ethoxy-ethanol* containing 3 g (20 mmol) of sodium iodide. 93.3 g (706 mmol) of diethyl malonate is then added, followed by a 25 ml. (dry) 2-ethoxy-ethanol rinse. Into the dropping funnel is placed 16.95 g (431.5 mmol) of 61.1% sodium hydride-mineral oil. The oil is removed by washing thrice with 80 ml portions of petroleum ether (each time suspending with a magnetic stirrer, allowing to settle and withdrawing the supernatant wash by syringe). The thus cleaned sodium hydride is protected from moisture in the dropping funnel, which is sealed with a rubber stopple and re-suspended by adding 100 ml of dry petroleum ether (b.p. 30°–60°), which suspension, is gradually added at such a rate to the vessel at −10° to 0°, with stirring so as to control the evolution of hydrogen gas.
*also called ethylene glycol monoethyl ether.

The mixture is gradually warmed (over a period of approx. 3 hr) with stirring to approx. 125°, while volatile solvents (petroleum ether and THF) collect and are removed via the trap. The suspension is stirred at approx. 125° for 92 hr. First 50 ml of toluene, then 300 ml of hexane are added as the reaction mixture is cooled to below 20°. 17.6 ml of glacial acetic acid (308 mmol) is injected, followed by the addition of excess water. After stirring-equilibration and settling of the aqueous salty phase it is removed by suction. The organic phase is gradually brought to a temperature of 137° under slight vacuum while solvents distill off to obtain about 60 ml of an oil (crude n-decyldimethylsilylpropylmalonic ester.

Step C, 6,6-dimethyl-6-sila-n-hexadecanoic acid

To the oily residue obtained in Step B is added 25.5 g of KOH (403 mmol) in 350 ml of ethanol, and the mixture is heated-stirred at reflux for 20 hr. To the resulting suspension 35 ml of water is added, followed by additional heating-stirring for 3 hr.

The mixture is slightly cooled and concentrated to low volume (near solid) in vacuo. Ice, petroleum ether, then excess con. hydrochloric acid are added with stirring to reach acidic pH. Approx. 200 ml of ether is added to aid separation of the organic phase. The aqueous phase is is drained, the organic phase is washed with 200 ml of saturated aqueous sodium chloride, three 200-ml portions of water, dried, filtered, concentrated to the crude product, which is fractionally distilled in high vacuo using a packed column to obtain the refined title product, b.p. 145°–140°/0.101–0.090 mm Hg.

Repeating the procedure of this example, but using in place of the 3-chloropropyl-dimethyl-chlorosilane used in Step A, 20.6 g of chloromethyl dimethyl chlorosilane, there is accordingly obtained 4,4-dimethyl-4-sila-n-tetradecanoic acid (b.p. 138°–140° at 0.135–125 mm Hg).

EXAMPLE 8
4-Sila-4,4-dimethyl-n-tetradecanoic Acid

Step A, Ethyl-4-sila-2-cyano-4,4-dimethyl-n-tetradecanoate

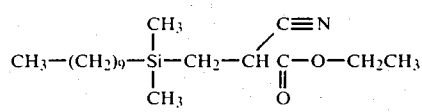

Under anhydrous conditions, 1.161 g (29.6 mmoles) of sodium hydride dispersed in mineral oil (61.1% NaH) is washed free of the oil by washing thrice with portions of hexane. The thus-washed sodium hydride is then added cautiously under a nitrogen atmosphere to a solution of 3.8 g (33.6 mmoles) of ethyl cyanoacetate and 9.6 g (28.2 mmoles) of n-decyl-dimethyl-iodomethylsilane in 20 ml of dry dimethyl formamide (which had been distilled from calcium hydride), with external cooling applied as necessary to avoid rapid temperature rise, but to allow prompt evolution of hydrogen gas from the reaction mixture. After addition is completed, the reaction is heated to 55°, with stirring for 1 hr. and then at 65° for 1.5 hr., then allowed to cool. The cooled mixture is diluted with hexane, then 4 drops of acetic acid (gl.) are added, and the mixture poured into cold water (about 15°). The organic layer is recovered and washed thrice with portions of water, dried over anh. sodium sulfate, filtered and concentrated by evaporating under vacuum to obtain an oily residue. The residue is distilled in a Kugelrohr apparatus to obtain the refined product of this step, at 105°–117° (air bath) and 0.100–0.095 mm Hg.

Step B, 2-Cyanoethyl-n-decyl-dimethyl-silane

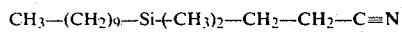

A mixture of 3.5 g of ethyl-4-sila-2-cyano-4,4-dimethyl-n-tetradecanoate (from Step A), 6 ml of acetic acid (gl.) and 4 ml. of concentrated hydrochloric acid is heated for 8 hr. in a bath at 120°, and by-products (eg ethyl acetate) are evaporated off. Vacuum is then applied and evaporation continued until a concentrate of mostly one phase remains. The concentrate is mixed with petroleum ether and water, and the organic phase recovered, washed with water, dried over anh. sodium sulfate, filtered and evaporated to obtain an oil. The oil is distilled in a kugelrohr apparatus to obtain the title product of this step as fraction collected at 106°–111° at 0.120–0.113 mm Hg, and then at 111°–164° at 0.113–0.130 mm Hg. The fractions are combined for use in step c, below.

Step C, 4-sila-4,4-dimethyl-n-tetradecanoic acid 2.1 g of 2-cyanoethyl-n-decyl-dimethyl silane is refluxed with 2 g of potassium hydroxide and 8 g of water for 88 hrs. with stirring. The mixture is cooled, acidified with 2 N hydrochloric acid, then extracted with methylene chloride. The organic phase is dried over anh. sodium sulfate, filtered, and then evaporated under vacuum to obtain the title product as an oily residue, which is refined by distillation in a Kugelrohr apparatus at 112°–116° at 0.110 to 0.105 mm Hg.

EXAMPLE 9

Repeating the procedure of steps A, B, C and D of Example 1, but using in place of the n-decyl bromide used therein, an approximately equivalent amount of:
(a) n-octyl bromide;
(b) t-butyl bromide;
(c) benzyl bromide; or
(d) phenyl bromide;
there is accordingly obtained:
(a) 6,6-dimethyl-6-sila-n-tetradecanoic acid;
(b) 6,6,7,7-tetramethyl-6-sila-n-octanoic acid;
(c) 6,6-dimethyl-6-sila-7-phenyl-n-heptanoic acid; and
(d) 6-methyl-6-phenyl-6-sila-heptanoic acid.

EXAMPLE 10

Employing the products (IV) of Example 9, according to the procedure of Step E of Example 1 there is accordingly obtained:
(a) 6,6-dimethyl-6-sila-n-tetradecanoyl-1'-benzyl-2'-phenylethylamide;
(b) 6,6,7,7-tetramethyl-6-sila-n-octanoyl-1'-benzyl-2'-phenylethylamide;
(c) 6,6-dimethyl-6-sila-7-phenyl-n-heptanoyl-1'-benzyl-2'-phenylethylamide; and
(d) 6-methyl-6-phenyl-6-sila-heptanoyl-1'-benzyl-2'-phenylethylamide.

EXAMPLE 11

Employing the products of Example 9 according to the procedure of Example 2 there is accordingly obtained:
(a) D,L-6,6-dimethyl-6-sila-n-tetradecanoyl-1'-phenyl-2'-p-tolyl-ethylamide;
(b) D,L-6,6,7,7-tetramethyl-6-sila-n-octanoyl-1'-phenyl-2-(p-tolyl)-ethylamide;
(c) D,L-6,6-dimethyl-7-phenyl-6-sila-n-heptanoyl-1'-phenyl-2-p-tolyl-ethylamide; and
(d) D,L-6-methyl-6-phenyl-6-sila-heptanoyl-1'-phenyl-2'-(p-tolyl)-ethylamide.

EXAMPLE 12

Repeating the procedure of Step A of Example 3, but using in place of the n-decyl bromide used therein, an approximately equivalent amount of phenyl bromide, there is accordingly obtained 5-methyl-5-phenyl-5-silahexanol, which upon treatment according to the methods of Step B of Example 3, and then Example 2, yields, first 5-methyl-5-phenyl-5-sila-hexanoic acid, and then D,L-5-methyl-5-phenyl-5-sila-hexanoyl-1'-phenyl-2'-p-tolyl-ethylamide.

Repeating the procedure of this example but using in place of the 1,1-dimethyl-1-sila-2-oxacyclohexane, used therein, an approximately equivalent amount of:
(a) 1-phenyl-1-methyl-1-sila-2-oxacyclohexane;
(b) 1-butyl-1-phenyl-1-sila-2-oxacyclohexane; and
(c) 1,1-diphenyl-1-sila-2-oxacyclohexane;
there is accordingly obtained
(a1) 5,5-diphenyl-5-sila-hexanol,
(a2) 5,5-diphenyl-5-sila-hexanoic acid and
(a3) D,L-5,5-diphenyl-5-sila-hexanoyl-1'-phenyl-2'-p-tolyl-ethylamide;
(b1) 5,5-diphenyl-5-sila-n-nonanol;
(b2) 5,5-diphenyl-5-sila-n-nonanoic acid; and
(b3) D,L-5,5-diphenyl-5-sila-n-nonanoyl-1'-phenyl-2'-p-tolyl-ethylamide; and
(c1) 5,5,5-triphenyl-5-sila-pentanol;
(c2) 5,5,5-triphenyl-5-sila-pentanoic acid; and
(c3) D,L-5,5,5-triphenyl-5-sila-pentanoyl-1'-phenyl-2'-p-tolyl-ethylamide.

EXAMPLE 13

Repeating the procedure of Steps A, B, C and D of Example 1 but using in place of the n-decyl bromide used therein, an approximately equivalent amount of benzyl bromide and in place of the (3-chloropropyl)-dimethyl-chlorosilane, using an approximately equivalent amount of benzyl-(3-chloropropyl)methyl-chlorosilane, there is accordingly, obtained as the corresponding compound IV, 6,6-dibenzyl-6-sila-heptanoic acid, which upon treatment according to Example 2 yields, accordingly, 6,6-dibenzyl-6-sila-heptanoyl-1'-phenyl-2'-p-tolyl-ethylamide.

EXAMPLE 14

Adopting the procedure of Example 2 and in place of the 1-phenyl-2-p-tolyl ethylamine used therein, using an approximately equivalent amount of the following amines (in free or salt form) as Compounds III:
(a) 1-amino-indane;
(b) DL-tryptophan ethyl ester, hydrochloride;
(c) (d,l) α-methylbenzylamine; (racemate);
(d) 2-methylaniline;
(e) 1-(p-methylbenzyl)-2-p-tolyl-ethylamine; or
(f) (+)-α-methylbenzylamine
there is accordingly obtained, respectively:
(a) N-(6,6-dimethyl-6-sila-hexadecanoyl)-1-indanylamide;
(b) N-6,6-dimethyl-6-sila-hexadecanoyl-tryptophan, ethyl ester,
(c) N-(6,6-dimethyl-6-sila-hexadecanoyl)-α-methylbenzylamide, (as a racemic mixture);
(d) N-(6,6-dimethyl-6-sila-hexadecanoyl)-o-methylphenylamide;
(e) N-(6,6-dimethyl-6-sila-hexadecanoyl)-1'-p-methylbenzyl-2'-p-tolyl-ethylamide, and
(f) (+)N-(6,6-dimethyl-6-sila-hexadecanoyl)-1'-phenylethylamide.

EXAMPLE 15

Adapting the procedure of Step C of Example 7, and employing an approximately equivalent amount of malonates listed as (a) to (e) of Example 6 in place of the dimethyl n-decyldimethyl-silylmethyl malonate used therein, there is accordingly obtained:
(a) 7,7-dimethyl-7-sila-heptadecanoic acid;
(b) 5,5-di-(n-hexyl)-5-sila-pentadecanoic acid;
(c) 7,7-dimethyl-7-sila-pentadecanoic acid;
(d) 11,11-di(n-propyl)-11-sila-pentadecanoic acid; and
(e) 7-phenyl-6,6-dimethyl-6-sila-heptanoic acid.

Adapting the procedures of Step E of Example 1 and Example 4 and employing the above listed silyl-carboxylic acids (IV) the corresponding analogous amides are obtained.

EXAMPLE 16

Following the procedure of Example 3, but using in step A, in place of the 1,1-dimethyl-1-sila-2-oxacyclohexane, an approximately equivalent amount of:
(a) 1,1-dimethyl-1-sila-2-oxacycloheptane
(b) 1,1-dimethyl-1-sila-2-oxacyclooctane; and
(c) 1,1-dimethyl-1-sila-2-oxacyclodecane;
there is accordingly obtained
(a1) 6,6-dimethyl-6-sila-n-hexadecanol; and
(a2) 6,6-dimethyl-6-sila-n-hexadecanoic acid;
(b1) 7,7-dimethyl-7-sila-n-heptadecanol; and (b2) 7,7-dimethyl-7-sila-n-heptadecanoic acid; and
(c1) 9,9-dimethyl-9-sila-n-nonadecanol; and
(c2) 9,9-dimethyl-9-sila-n-nonadecanoic acid.

Adapting the procedures of Step E of Example 1 and Example 4 and employing the above listed silyl-carboxylic acids (IV) the corresponding analogous amides are obtained.

EXAMPLE 17

Adapting the procedure of Example 8, and employing in place of the n-decyl dimethyl-iodomethylsilane used in Step A therein an approximately equivalent amount of:
(a) n-decyl-dimethyl-iodoethylsilane; or
(b) n-decyl-dimethyl-iodopropylsilane;
there is accordingly obtained:
(a) 5,5-dimethyl-5-sila-n-pentadecanoic acid; and
(b) 6,6-dimethyl-6-sila-n-hexadecanoic acid.

What is claimed is:

1. A compound of the formula:

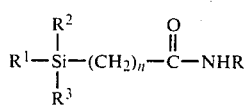

wherein n is a whole integer of from 3 to 20, each of $R^1$, $R^2$ and $R^3$ is, independently, either (a) alkyl having from 1 to 22 carbon atoms; or (b) a radical of the formula

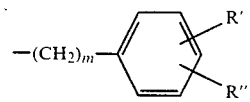

in which m is 0, 1 or 2, and each of R' and R'' is, independently, a hydrogen atom, alkyl having from 1 to 3 carbon atoms, alkoxy having from 1 to 3 carbon atoms, or halo having an atomic weight of from about 19 to 127; provided that the sum of n and the number of carbon atoms in any one of $R^1$, $R^2$ or $R^3$ is not greater than 34 when any of $R^1$, $R^2$ or $R^3$ is of type (a); and R is of type (a) an aralkyl-type radical of the structure:

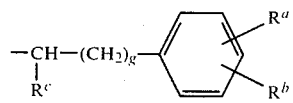

wherein g is 0, 1 or 2;
$R^a$ is a hydrogen atom, halo having an atomic weight of from about 19 to 127, alkoxy having from 1 to 4 carbon atoms, or alkyl having from 1 to 4 carbon atoms, or trifluoromethyl;
$R^b$ is a hydrogen atom, alkyl having from 1 to 3 carbon atoms, alkoxy having from 1 to 3 carbon atoms, or halo having an atomic weight of from about 19 to 36; and
$R^c$ is subtype (i) a hydrogen atom; subtype (ii) a radical of the structure

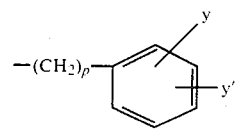

in which p is 0, 1 or 2, and
y is a hydrogen atom, halo having an atomic weight of from about 19 to 127, alkoxy having from 1 to 4 carbon atoms, or alkyl having from 1 to 4 carbon atoms; and
y' is a hydrogen atom, alkoxy having from 1 to 3 carbon atoms, alkyl having from 1 to 3 carbon atoms, or halo having an atomic weight of from about 19 to 36; or
subtype (iii) alkyl having from 1 to 8 carbon atoms; or R is of type (b) a phenyl-type radical of the structure

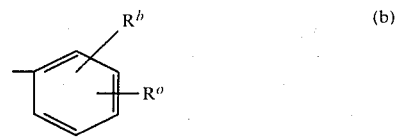

in which $R^b$ is as defined above, and
$R^o$ is a hydrogen atom, halo having an atomic weight of from about 19 to 127, ie. alkoxy having from 1 to 4 carbon atoms, or alkyl having from 1 to 4 carbon atoms; or
$R^o$ is a radical of the structure $R^f$:

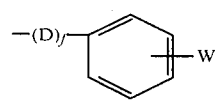

in which D is —$CH_2$— or —O—;
f is 0 or 1; and
W is a hydrogen atom, halo having an atomic weight of from about 19 to 80, alkoxy having from 1 to 3 carbon atoms, or alkyl having from 1 to 3 carbon atoms; or R is of type (c) an indolyl radical of the structure:

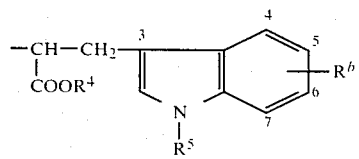

wherein $R^b$ is as defined above;
$R^4$ is alkyl having from 1 to 8 carbon atoms or benzyl (unsubstituted); and
$R^5$ is a hydrogen atom, alkyl having from 1 to 8 carbon atoms or benzyl (unsubstituted); or
R is (d) a benzocycloalkyl radical of the structure:

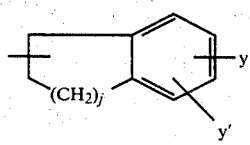

wherein y and y' are as defined above; and j is a whole integer of from 1 to 4.

2. A compound of claim 1, in which each of $R^1$, $R^2$ and $R^3$ is of type (a).

3. A compound of claim 1, in which any of $R^1$, $R^2$, and $R^3$ is of type (b).

4. A compound of claim 1 in which R is of type (a).

5. A compound of claim 1 in which R is of type (b).

6. A compound of claim 1 in which R is of type (c).

7. A compound of claim 1 in which R is of type (d).

8. A compound of claim 1 in which $R^1$ and $R^2$ are both methyl.

9. The compound of claim 1 which is D,L-5,5-dimethyl-5-sila-pentadecanoyl-1'-phenyl-2'-tolyl-ethylamide.

10. The compound of claim 1 which is 6,6-dimethyl-6-sila-n-hexadecanoyl-1'-benzyl-2'-phenyl-ethylamide.

11. The compound of claim 1 which is D,L-6,6-dimethyl-6-sila-n-hexadecanoyl-1'-phenyl-2'-p-tolyl-ethylamide.

12. The compound of claim 1 which is 5,5-dimethyl-5-sila-n-pentadecanoyl-1'-benzyl-2'-phenyl ethylamide.

13. A method of reducing the cholesterol ester content of an arterial wall, in a mammal in need of such treatment, comprising administering a total cholesterol ester-reducing amount of a compound of claim 1 to said mammal.

14. A pharmaceutical composition suitable for reducing the cholesterol ester content of an arterial wall of a mammal comprising a cholesterol ester-reducing effective amount of a compound of claim 1 and a non-toxic pharmaceutically-acceptable carrier.

15. A method of claim 13 in which the compound is present in an amount of from about 10 milligrams to about 5,000 milligrams.

16. A method of claim 13 in which the compound is present in an amount of from about 10 milligrams to about 2,000 milligrams.

17. A method of claim 13 in which the compound is D,L-5,5-dimethyl-5-sila-n-pentadecanoyl-1'-phenyl-2'-p-tolyl-ethylyamide.

18. A composition of claim 9 in which the compound is present in an amount of from about 2.5 milligrams to about 2,500 milligrams.

19. A composition of claim 14 in a solid form.

20. A composition of claim 14 in which the carrier is solid.

21. A composition of claim 14 in which the carrier is liquid.

22. A composition of claim 14 in which the compound is D,L-5,5-dimethyl-5-sila-n-pentadecanoyl-1'-phenyl-2'-p-tolyl-ethylamide.

* * * * *